(12) United States Patent
Ceze et al.

(10) Patent No.: US 11,164,661 B2
(45) Date of Patent: Nov. 2, 2021

(54) INTEGRATED SYSTEM FOR NUCLEIC ACID-BASED STORAGE AND RETRIEVAL OF DIGITAL DATA USING KEYS

(71) Applicant: University of Washington, Seattle, WA (US)

(72) Inventors: Luis Henrique Ceze, Seattle, WA (US); Georg Seelig, Seattle, WA (US)

(73) Assignee: UNIVERSITY OF WASHINGTON, Seattle, WA (US)

(*) Notice: Subject to any disclaimer, the term of this patent is extended or adjusted under 35 U.S.C. 154(b) by 1059 days.

(21) Appl. No.: 15/565,372

(22) PCT Filed: Apr. 8, 2016

(86) PCT No.: PCT/US2016/026726
§ 371 (c)(1),
(2) Date: Feb. 12, 2018

(87) PCT Pub. No.: WO2016/164779
PCT Pub. Date: Oct. 13, 2016

(65) Prior Publication Data
US 2018/0068060 A1 Mar. 8, 2018

Related U.S. Application Data

(60) Provisional application No. 62/145,655, filed on Apr. 10, 2015, provisional application No. 62/257,661, filed on Nov. 19, 2015.

(51) Int. Cl.

| | |
|---|---|
| G16B 50/30 | (2019.01) |
| G06F 16/00 | (2019.01) |
| G16B 30/00 | (2019.01) |
| G16B 50/00 | (2019.01) |
| G11C 13/02 | (2006.01) |
| G16B 50/40 | (2019.01) |
| G16B 50/20 | (2019.01) |
| G16B 25/20 | (2019.01) |
| G11C 7/00 | (2006.01) |
| G06F 16/901 | (2019.01) |
| G06F 16/90 | (2019.01) |
| G16B 25/00 | (2019.01) |
| G11C 29/00 | (2006.01) |
| G06F 11/00 | (2006.01) |

(52) U.S. Cl.
CPC ............ *G16B 50/30* (2019.02); *G06F 16/00* (2019.01); *G06F 16/90* (2019.01); *G06F 16/901* (2019.01); *G11C 7/00* (2013.01); *G11C 13/02* (2013.01); *G16B 25/20* (2019.02); *G16B 30/00* (2019.02); *G16B 50/00* (2019.02); *G16B 50/20* (2019.02); *G16B 50/40* (2019.02); *B01J 2219/00722* (2013.01); *G06F 11/00* (2013.01); *G11C 29/00* (2013.01); *G16B 25/00* (2019.02)

(58) Field of Classification Search
None
See application file for complete search history.

(56) References Cited

U.S. PATENT DOCUMENTS

| | | |
|---|---|---|
| 6,322,983 B1 | 11/2001 | Burgoyne |
| 8,431,340 B2 | 4/2013 | Jovanovich et al. |
| 2005/0053968 A1 | 3/2005 | Bharadwaj et al. |

FOREIGN PATENT DOCUMENTS

| | | |
|---|---|---|
| WO | 2003/025123 A2 | 3/2003 |
| WO | 2013/178801 A2 | 12/2013 |
| WO | 2014/014991 A2 | 1/2014 |

OTHER PUBLICATIONS

International Search Report and Written Opinion dated Jul. 15, 2016, issued in corresponding International Application No. PCT/US2016/026726, filed Apr. 8, 2016, 15 pages.
Goldman et al., "Toward Practical High-Capacity Low-Maintenance Storage of Digital Information in Synthesised DNA," Nature, Feb. 7, 2013; 494(7435): 77-80. doi: 10.1038/nature11875, pp. 1-9.
Paunescu et al., "Reversible DNA Encapsulation in Silica to Produce ROS-Resistant and Heat-Resistant Synthetic DNA 'Fossils'," Nature Protocols, vol. 8, No. 12, 2013, pp. 2440-2448.
Shrivastava et al., "Data Storage in DNA," International Journal of Electrical Energy, vol. 2, No. 2, Jun. 2014, pp. 119-122.
Wan et al., "Green Technologies for Room Temperature Nucleic Acid Storage," Curr. Issues Mol. Biol. vol. 12, 2010, pp. 135-142.
Grass, et al., "Robust Chemical Preservation of Digital Information on DNA in Silica with Error-Correcting Codes," Angew. Chem. Int. Ed. 54:2552-2555 (2015).

(Continued)

*Primary Examiner* — G Steven Vanni
(74) *Attorney, Agent, or Firm* — Christensen O'Connor Johnson Kindness PLLC

(57) ABSTRACT

In some embodiments, systems and methods for storing and/or retrieving digital information in a nucleic acid library are provided. In some embodiments, an integrated system comprising a nucleic acid synthesis device, a nucleic acid sequencing device, a computing device, and a nucleic acid library is provided. In some embodiments, a write request that associates a value with a key is received by the system, the system synthesizes nucleic acid molecules associated with the request, and stores the nucleic acid molecules in the nucleic acid library. In some embodiments, a read request for a key is received by the system, and the system sequences nucleic acid molecules from the nucleic acid library that are associated with the key.

18 Claims, 9 Drawing Sheets

(56) References Cited

OTHER PUBLICATIONS

Paunescu, et al., "Protection and Deprotection of DNA-High-Temperature Stability of Nucleic Acid Barcodes for Polymer Labeling," Angew. Chem. Int. Ed. 52:4269-4272 (2013).

Allen School News, "UW CSE and Microsoft Research Efforts to Use DNA for Data Storage Featured in The New York Times," University of Washington, Seattle, Dec. 3, 2015, <https://news.cs.washington.edu/2015/12/03/uw-cse-and-microsoft-research-efforts-to-use-dna-for-data-storage-featured-in-the-new-york-times/> [retrieved May 13, 2019], 3 pages.

Boyle, A., "Encoding Data in DNA for Millennia? UW and Microsoft Research Are on It," GeekWire, Dec. 4, 2015, <https://www.geekwire.com/2015/encoding-data-into-dna-molecules-uw-microsoft-research-on-it/> [retrieved May 13, 2019], 4 pages.

Church, G.M., et al., "Next-Generation Digital Information Storage in DNA," Science 337(6102):1628, Sep. 2012, 1 page.

Goldman, N., et al., "Towards practical, High-Capacity, Low-Maintenance Information Storage in Synthesized DNA," Nature 494:77-80, Feb. 2013.

Hossein Tabatabaei Yazdi, S.M., et al., "A Rewritable, Random-Access DNA-Based Storage System," Scientific Reports 5:14138, Sep. 2015, pp. 1-10.

Markoff, J., "Data Storage on DNA Can Keep it Safe for Centuries," The New York Times, Dec. 3, 2015, <https://www.nytimes.com/2015/12/04/science/data-storage-on-dna-can-keep-it-safe-for-centuries.html> [retrieved May 13, 2019], 6 pages.

Yong, E., "Synthetic Double-Helix Faithfully Stores Shakespear's Sonnets," Nature News, Jan. 23, 2013, <https://www.nature.com/news/synthetic-double-helix-faithfully-stores-shakespeare-s-sonnets-1.12279> [retrieved May 13, 2019], 2 pages.

INTEGRATED SYSTEM FOR NUCLEIC ACID-BASED STORAGE AND RETRIEVAL OF DIGITAL DATA USING KEYS

STATEMENT OF GOVERNMENT LICENSE RIGHTS

This invention was made with Government support under Grant CCF 1409831 awarded by the National Science Foundation (NSF). The Government has certain rights in the invention.

BACKGROUND

With the ever growing data production in the world, a sustainable and dense storage mechanism for digital information is desired. Current systems based on electrical, magnetic, or optical phenomena have inherent limitations in information density and long-term storage fidelity.

Recent research proposed the idea of storing digital information in synthetic DNA molecules, promising density and durability. Experimental demonstrations have shown that such a storage principle is feasible in principle. However, these results had shortcomings that prevent them from being actually useful in practice. For example, the previous experiments only offer sequential access to stored data. In other words, it is necessary to read the entirety of the stored data to retrieve a subset of desired data. As another example, the read/write processes were not integrated into a single device.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In some embodiments, a system for storing digital information in and retrieving digital information from a nucleic acid library is provided. The system comprises a nucleic acid synthesis device, a nucleic acid sequencing device, a nucleic acid storage medium configured to store a nucleic acid library, and at least one computing device. The at least one computing device is configured to provide an external interface, an address determination engine, a sequence generation engine, and a data extraction engine. The external interface is configured to receive a read request, the read request including a first key. The address determination engine is configured to determine a first address based on the first key. The sequence generation engine is configured to determine a first primer sequence based on the first address; determine at least one nucleic acid sequence representing the first primer sequence; and provide the at least one nucleic acid sequence representing the first primer sequence to the nucleic acid synthesis device for synthesis of at least one first primer molecule. The data extraction engine is configured to receive nucleic acid sequence information from the nucleic acid sequencing device representing nucleic acid molecules from the nucleic acid storage medium as amplified using the at least one first primer molecule; and extract a first value from the received nucleic acid sequence information, wherein the first value is associated with the first key.

In some embodiments, a method of managing digital information stored in a nucleic acid library is provided. A computing device receives a read request including a first key. The computing device calculates a first primer sequence based on the first key. The computing device generates at least one nucleic acid sequence that represents the first primer sequence. The computing device provides the at least one nucleic acid sequence to a nucleic acid synthesis device for synthesis of at least one first primer molecule. The computing device receives nucleic acid sequence information from a nucleic acid sequencing device representing nucleic acids from a nucleic acid storage medium amplified using the at least one first primer molecule. The computing device extracts a first value associated with the first key from the received nucleic acid sequence information. The computing device transmits the first value in response to the read request.

In some embodiments, a nontransitory computer-readable medium having computer-executable instructions stored thereon is provided. The instructions, in response to execution by one or more processors of a computing device, cause the computing device to perform actions for managing digital information stored in a nucleic acid library. The actions comprise receiving, by the computing device, a write request including a first key and a first value; calculating, by the computing device, a first primer sequence associated with the first key; generating, by the computing device, at least one nucleic acid sequence that includes a first primer target region and a region representing the first value, wherein the first primer target region represents a sequence complementary to the first primer sequence; and providing, by the computing device, the at least one nucleic acid sequence that includes the first primer target region and the region representing the first value to a nucleic acid synthesis device for synthesis of at least one nucleic acid molecule.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Figure 1:
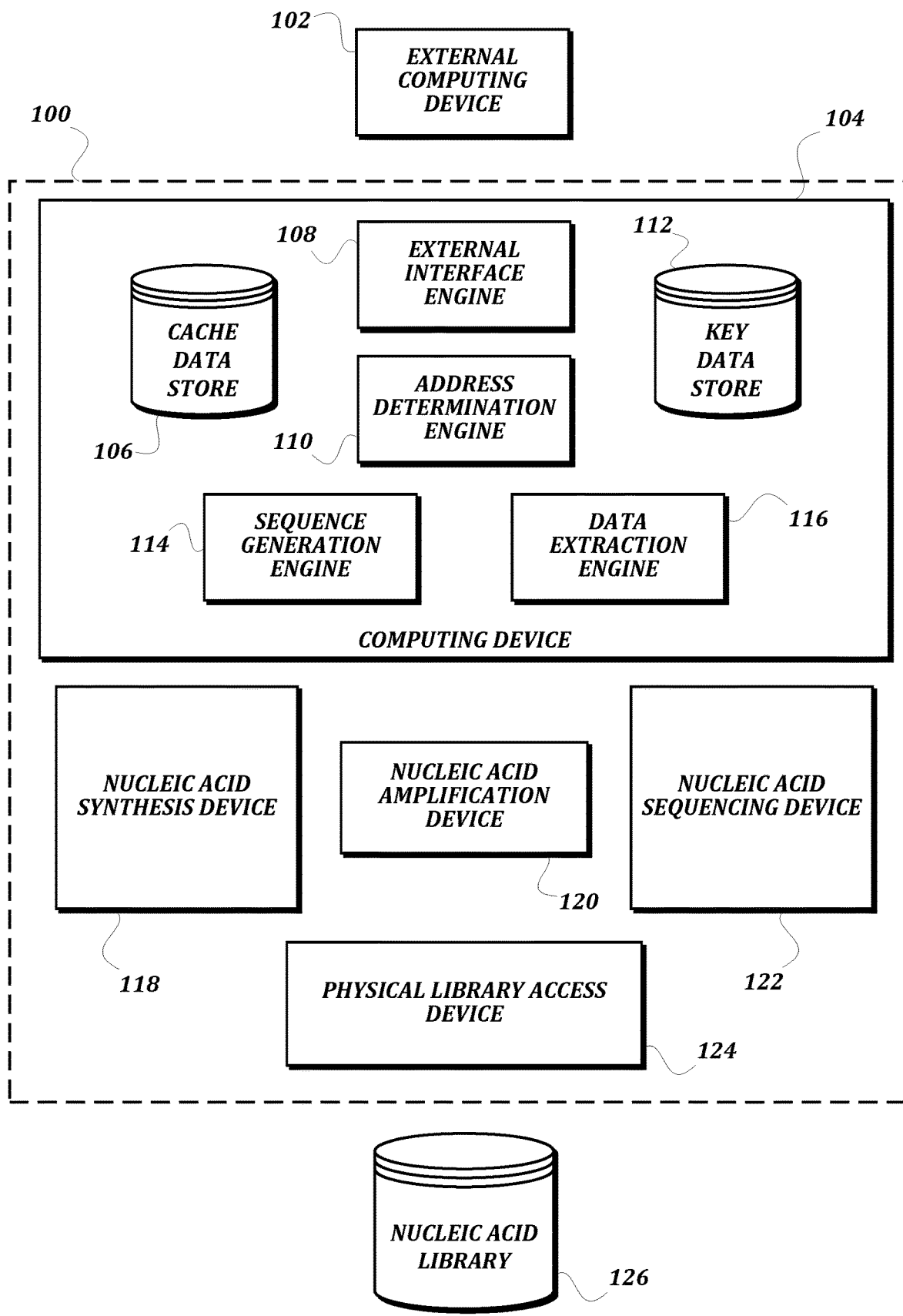
FIG. 1 is a block diagram that illustrates an exemplary embodiment of a digital data storage system according to various aspects of the present disclosure.

In some embodiments, systems and methods for storing and/or retrieving digital information in a nucleic acid library are provided. In some embodiments, an integrated system comprising a nucleic acid synthesis device, a nucleic acid sequencing device, a computing device, and a nucleic acid library is provided. In some embodiments, a write request that associates a value with a key is received by the system, the system synthesizes nucleic acid molecules associated with the request, and stores the nucleic acid molecules in the nucleic acid library. In some embodiments, a read request for a key is received by the system, and the system sequences nucleic acid molecules from the nucleic acid library that are associated with the key.

As used herein, the terms "nucleic acid" and "polynucleotides" refer to biopolymers that are made from monomer units referred to as "nucleotides." Typically, each nucleotide is composed of a 5-carbon sugar, a phosphate group, and a nitrogenous base (also referred to as "nucleobase"). The structure of the sugar component typically defines to the type of nucleic acid polymer. The nucleotide monomers link up to form a linear sequence of the nucleic acid polymer. Nucleic acids encompassed by the present disclosure can include deoxyribonucleic acid (DNA), ribonucleic acid (RNA), cDNA or a synthetic nucleic acid known in the art, such as peptide nucleic acid (PNA), glycerol nucleic acid (GNA), threose nucleic acid (TNA), locked nucleic acid (LNA) or other synthetic polymers with nucleotide side chains, or any combination thereof. Nucleic acid molecules can be single stranded or double stranded (with complementary single-stranded polynucleotide chains hybridizing by base pairing of the individual nucleobases). Typically cDNA, RNA, GNA, TNA or LNA are single stranded. DNA can be either double stranded (dsDNA) or single stranded (ssDNA).

Nucleotide subunits of nucleic acids can be naturally occurring, artificial, or modified. As indicated above, nucleotide typically contains a nucleobase, a sugar, and at least one phosphate group. The nucleobase is typically heterocyclic. Suitable nucleobases include the canonical purines and pyrimidines, and more specifically adenine (A), guanine (G), thymine (T) (or typically in RNA, uracil (U) instead of thymine (T)), and cytosine (C). The sugar is typically a pentose sugar. Suitable sugars include, but are not limited to, ribose and deoxyribose. The nucleotide is typically a ribonucleotide or deoxyribonucleotide. The nucleotide typically contains a monophosphate, diphosphate or triphosphate. These are generally referred to herein as nucleotides or nucleotide residues to indicate the subunit. Without specific identification, the term nucleotides, nucleotide residues, and the like, is not intended to imply any specific structure or identity. As indicated above, the nucleic acids of the present disclosure can also include synthetic variants of DNA or RNA. "Synthetic variants" encompasses nucleic acids incorporating known analogs of natural nucleotides/nucleobases that can hybridize to nucleic acids in a manner similar to naturally occurring nucleotides. Exemplary synthetic variants include peptide nucleic acids (PNAs), phosphorothioate DNA, locked nucleic acids, and the like. Modified or synthetic nucleobases and analogs can include, but are not limited to, 5-Br-UTP, 5-Br-dUTP, 5-F-UTP, 5-F-dUTP, 5-propynyl dCTP, 5-propynyl-dUTP, diaminopurine, S2T, 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N 6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-D46-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, 2,6-diaminopurine and the like. Persons of ordinary skill in the art can readily determine what base pairings for each modified nucleobase are deemed a base-pair match versus a base-pair mismatch.

FIG. 1 is a block diagram that illustrates an exemplary embodiment of a digital data storage system according to various aspects of the present disclosure. As illustrated, the digital data storage system 100 includes a computing device 104, a nucleic acid synthesis device 118, a nucleic acid amplification device 120, a nucleic acid sequencing device 122, and a physical library access device 124. In some embodiments, the nucleic acid amplification device 120 may be optional or unused. In some embodiments, the computing device 104, nucleic acid synthesis device 118, nucleic acid amplification device 120 (if present), nucleic acid sequencing device 122, and physical library access device 124 are located within a housing of a size appropriate for placement on a desktop or lab bench. In some embodiments, the physical library access device 124 may be partially or completely outside of the housing, while the nucleic acid amplification device 120 (if present), the computing device 104, the nucleic acid synthesis device 118, and the nucleic acid sequencing device 122 are inside of the housing.

The nucleic acid synthesis device 118 is configured to receive data representing nucleic acid sequences, and to synthesize nucleic acid molecules that embody the received nucleic acid sequences. Some non-limiting examples of nucleic acid synthesis devices 118 include solid support devices including in column, multi-well plate, and array formats. The nucleic acid synthesis device 118 may use techniques including, but not limited to, electrical, optical, or chemical control. For example, the nucleic acid synthesis device 118 can implement the synthesis in a solid-phase approach using phosphoramidite method and phosphoramidite building blocks derived from protected 2'-deoxynucleosides (dA, dC, dG, and T), ribonucleosides (A, C, G, and U), or chemically modified nucleosides, e.g. LNA, BNA. The nucleosides building blocks are sequentially coupled to the growing oligonucleotide chain in the order required by the sequence of the product. Upon the completion of the chain assembly, the product is released from the solid phase to solution and deprotected.

The nucleic acid sequencing device 122 is configured to determine the order of nucleobases in a polynucleotide, and thus to determine nucleic acid sequences embodied by nucleic acid molecules. Any device capable of determining the order of nucleobases in a polynucleotide may be used as a nucleic acid sequencing device 122, and include devices capable of performing, for example, Maxam-Gilbert or chemical sequencing, Sanger sequencing, shotgun sequencing, bridge PCR, massively parallel signature sequencing, polony sequencing, 454 pyrosequencing, Illumina dye sequencing, ion semiconductor sequencing, DNA nanoball sequencing, heliscope single molecule sequencing, single molecule real time sequencing, solid state nanopore sequencing, and/or protein-based nanopore sequencing. Such devices can include but are not limited to Illumina MiSeq devices, Illumina HiSeq devices, Oxford Nanopore devices, and others known in the art.

The nucleic acid amplification device 120 is configured to amplify nucleic acid molecules for use by the digital data storage system 100. As used herein, "amplifying" refers to producing copies of a nucleic acid molecule through one or more repeated rounds of primed enzymatic synthesis, where a strand of nucleic acid (i.e., "primer") complementary to a single stranded target nucleic acid can "prime" the enzymatic extension of the complementary strand based on target template. In some embodiments, amplifying includes one or more of the polymerase chain reaction (PCR), rolling circle replication, loop-mediated isothermal amplification (LAMP), helicase dependent amplification (HDA), and/or any other suitable technique. In some embodiments, the nucleic acid amplification device 120 includes a PCR thermal cycler.

If a housing is present around the digital data storage system 100, the nucleic acid library 126 may be contained inside or outside the housing. The physical library access device 124 is configured to store nucleic acid molecules in, and retrieve nucleic acid molecules from, a nucleic acid library 126. For example, the physical library access device 124 can include robotic arms equipped with a pipette or similar device for temporary holding of nucleic acids to physically move the nucleic acids to and from the nucleic acid library 126. The nucleic acid storage library 126 can be configured to hold and store the nucleic acids in any appropriate configuration or form. For example, R. N. Grass, et al., *Angew. Chem. Int. Ed.* 54:2552-2555 (2015), incorporated herein by reference in its entirety, describes several applicable "dry" approaches for long term nucleic acid storage. For example, the nucleic acid storage library 126 may include solid supports such as beads or microarrays. In some embodiments, nucleic acid molecules can be immobilized on solid supports in spatially defined physical locations that can be addressed separately from other nucleic acid molecules also stored in the nucleic acid storage library 126. In some embodiments, the nucleic acid molecules may be stored in impregnated filter paper. See, e.g., L. A. Burgoyne, U.S. Pat. No. 6,322,983, incorporated herein by reference in its entirety. In some embodiments, the nucleic acid molecules may be stored using technologies such as QIAsafe® (QIAGEN, Venlo, Netherlands), which is based on a biopolymer technology that mimics the anhydrous vitreous state of nucleic acids in seeds. See, e.g., E. Wan, et al., *Curr. Issues Mol. Biol.* 12:135-142 (2010), incorporated herein by reference in its entirety. In some embodiments, the nucleic acid molecules may be stored using a synthetic silica fossilization technology, such as described in D. Paunescu, et al., *Angew. Chem. Int. Ed.,* 52:4269-4272 (2013); D. Paunescu, et al., *Angew. Chem.* 125:4364-4368 (2013); and D. Paunescu, et al., *Nat. Protoc.* 8:2440-2448 (2013), each of which is incorporated herein by reference in its entirety. In some embodiments, the nucleic acid storage library 126 may include lyophilized nucleic acids that can be addressed or accessed by hydrating or reconstituting the nucleic acids and removing an aliquot for amplification, sequencing, and/or other analysis. In yet other embodiments, the nucleic acid storage library 126 can include a freezer appliance to maintain low temperatures (e.g., ~−20° C. or lower, such as to ~−80° C.) to further stabilize the nucleic acids stored therein for long term storage.

The computing device 104 may be any suitable computing device as described below in FIG. 6, such as a desktop computing device, a server computing device, a rackmount computing device, an embedded computing device, a laptop computing device, and/or the like. As illustrated, the computing device 104 is configured to provide an external interface engine 108, an address determination engine 110, a sequence generation engine 114, and a data extraction engine 116. In general, the word "engine," as used herein, refers to logic embodied in hardware or software instructions, which can be written in a programming language, such as C, C++, COBOL, JAVA™, PHP, Perl, HTML, CSS, JavaScript, VBScript, ASPX, Microsoft .NET™, and/or any other programming language. An engine may be compiled into executable programs or written in interpreted programming languages. Engines may be callable from other engines or from themselves. Generally, the engines described herein refer to logical modules that can be merged with other engines, or can be divided into sub-engines. The engines can be stored in any type of computer-readable medium or computer storage device and be stored on and executed by one or more general purpose computers, thus creating a special purpose computer configured to provide the engine.

The external interface engine 108 is configured to provide one or more interfaces via which an external computing device 102 can access functionality of the digital data storage system 100. The communication between the external interface engine 108 and the external computing device 102 includes the processing of write requests and read requests, which are described in further detail below. In some embodiments, the external interface engine 108 may provide an application programming interface (API) that allows the external computing device 102 to programmatically transmit read and write requests to the digital data storage system and receive appropriate results. In some embodiments, the external interface engine 108 may generate a graphical user interface (GUI) such as a web page or other interface that allows read and/or write requests to be processed. In some embodiments, the external interface engine 108 may provide a low-level interface, such as a USB interface, that allows the functionality of the digital data storage system 100 to be accessed in ways similar to that to other USB-based storage devices.

The external computing device 102 may be any suitable computing device, such as a desktop computing device, laptop computing device, tablet computing device, and/or the like. In some embodiments, the communication technology used to connect the external computing device 102 to the external interface engine 108 may be a local communication technology, such as USB, FireWire, eSATA, and/or the like. In some embodiments, the communication technology used to connect the external computing device 102 to the external interface engine 108 may use any suitable wired or wireless networking technology, including but not limited to Bluetooth, WiFi, infrared, 3G, 4G, LTE, NFC, Ethernet, and/or the like.

The address determination engine 110 is configured to determine addresses for storing and/or retrieving nucleic acid molecules within the nucleic acid library 126 based on keys received by the external interface engine 108. The sequence generation engine 114 is configured to generate nucleotide sequences to represent digital information, including but not limited to addresses, payloads, and sub-addresses. The sequence generation engine 114 provides the nucleotide sequences to the nucleic acid synthesis device 118 for synthesizing nucleic acid molecules that embody the nucleotide sequences. The data extraction engine 116 is configured to reconstruct digital information that includes addresses, payloads, and sub-addresses, and thereby reconstruct values associated with keys, based on sequence information received from the nucleic acid sequencing device 122. Further details regarding the operation of these components are provided below.

The computing device 104 also includes a cache data store 106 and a key data store 112. The cache data store 106 is configured to store keys and values that have recently been stored in or retrieved from the nucleic acid library 126. The key data store 112 is configured to store key records that each include an association between a key and a physical location identifier. In some embodiments, the cache data store 106 and/or the key data store 112 may be optional. Further details regarding the use of the cache data store 106 and the key data store 112 are provided below.

As understood by one of ordinary skill in the art, a "data store" as described herein may be any suitable device configured to store data for access by a computing device. One example of a data store is a highly reliable, high-speed relational database management system (RDBMS) executing on the computing device 104. However, any other suitable storage technique and/or device capable of quickly and reliably providing the stored data in response to queries may be used, such as a key-value store, an object database, and/or the like. Further, one or more computing devices providing the data store may be accessible over a network instead of part of the computing device 104, or may be provided as a cloud-based service. A data store may also include data stored in an organized manner on a computer-readable storage medium, as described further below. In some embodiments, the computer-readable storage medium on which the data of the data store is stored may be internal to the computing device 104, such as on a hard disk drive or other device, while in some embodiments, the computer-readable storage medium may be external to the computing device 104 and accessible via a cable such as a USB cable, FireWire cable, eSATA cable, and/or the like. Another example of a data store suitable for use with embodiments of the present disclosure is a file system or database management system that stores data in files (or records) on a computer-readable medium such as flash memory, random access memory (RAM), hard disk drives, and/or the like. One of ordinary skill in the art will recognize that separate data stores described herein may be combined into a single data store, and/or a single data store described herein may be separated into multiple data stores, without departing from the scope of the present disclosure.

Figure 2A:
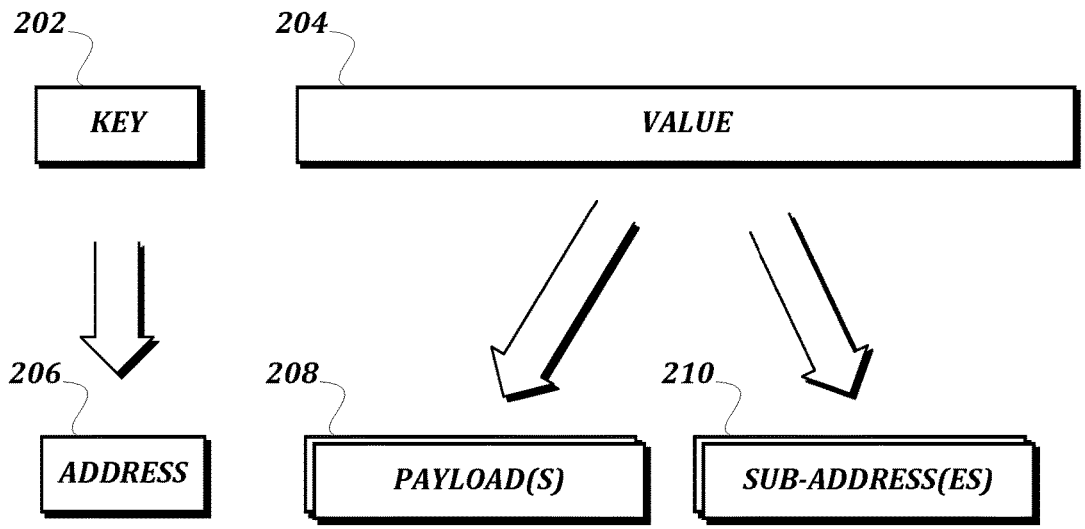
FIG. 2A is a schematic diagram that illustrates an exemplary embodiment of the transformation of a key and a value for storage in the digital data storage system according to various aspects of the present disclosure.

FIG. 2A is a schematic diagram that illustrates an exemplary embodiment of the transformation of a key and a value for storage in the digital data storage system according to various aspects of the present disclosure. The digital data storage system 100 stores and retrieves a value 204 using an associated key 202. Both the key 202 and the value 204 may be any type of digital data. In some embodiments, the key 202 may be a globally unique identifier (GUID), a uniform resource locator (URL), a string, an integer, or any other type of data that can uniquely identify the value 204. The value 204 may be any type of structured or unstructured digital data of any size. The key 202 is known to the external computing device 102, and is used by the external computing device 102 to submit the value 204 to the external interface engine 108 for storage, or to retrieve the value 204 from the external interface engine 108.

Within the digital data storage system 100, the key 202 is associated with an address 206, and the value 204 is associated with one or more payloads 208 and sub-addresses 210. In some embodiments, the digital data storage system 100 works with nucleic acid molecules of a limited maximum size in order to increase the probability of successful synthesis and/or sequencing based on the technologies utilized. For example, in some embodiments, a maximum nucleic acid molecule size between 150-200 nucleotides is used. In some embodiments, a fixed number of nucleotides may be reserved for use as the address 206. For example, in some embodiments 20 or 2×20 nucleotides may be reserved to represent the length of a typical PCR primer or primer pair to be used to encode the address 206. In some embodiments, a variable number of nucleotides may be reserved for use as the address 206, which is then terminated by a predetermined sequence of nucleotides to indicate a transition to the payload 208 or sub-address 210 portion. The remainder of the nucleic acid molecule within the maximum size may be used to store the value 204 as a payload 208. If the value 204 is too large to be stored within a single payload 208, then the value 204 is broken up into multiple payloads 208, and each of the multiple payloads 208 is associated with a different sub-address 210 in a separate nucleic acid molecule to allow the value 204 to be re-assembled from multiple molecules. See, e.g., Church, et al., WO 2014/014991 and Goldman et al., *Nature* 494:77-80 (2013), each of which is incorporated herein by reference in its entirety.

Using a fixed number of nucleotides for the address 206 establishes an address space for the keys. The address determination engine 110 determines an address 206 within the address space that is associated with each key 202. Any suitable technique for determining the address 206 associated with a key 202 may be used. For example, in some embodiments, a maximum size may be set for the key 202 that matches the amount of data that may be stored in number of nucleotides usable for the address 206, and so the key 202 may directly map to the address 206. As another example, in some embodiments, a hash function may be used to map keys 202 of arbitrary lengths to addresses 206 within the address space. In such cases, known techniques may be used to handle hash collisions, though with a large enough number of nucleotides used for the address, hash collisions should be rare.

Figure 2B:
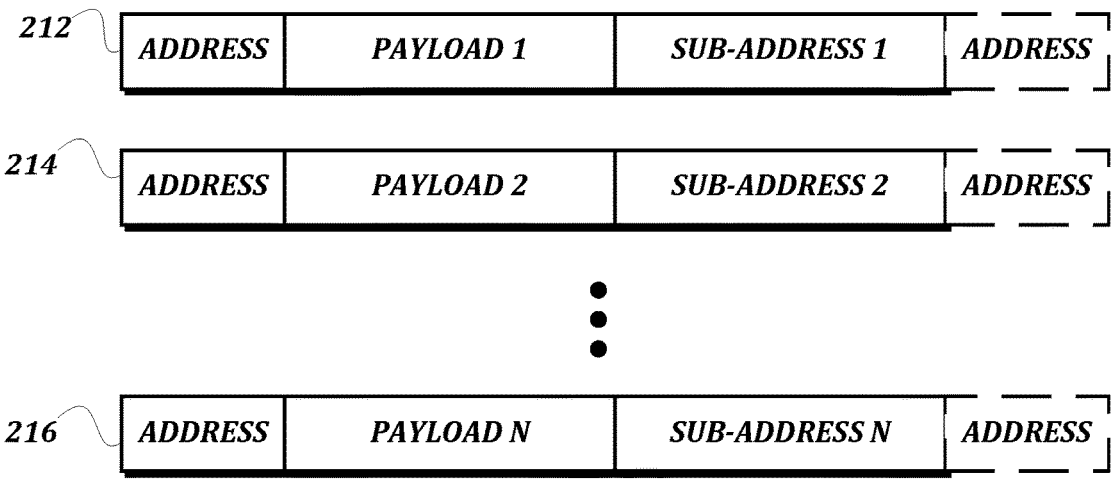
FIG. 2B is a schematic diagram that illustrates an exemplary embodiment of multiple nucleic acid sequences used to store a single value in the digital data storage system according to various aspects of the present disclosure.

FIG. 2B is a schematic diagram that illustrates an exemplary embodiment of multiple nucleic acid sequences used to store a single value in the digital data storage system according to various aspects of the present disclosure. This figure illustrates an example where the value 204 was too large to fit within a single payload 208, and so multiple molecules 212-216 had to be used. In each of the N molecules 212-216, the same address is used so that all of the N molecules may be analyzed at once. Each separate payload is associated with a different sub-address that indicates where in the overall value 204 the particular payload belongs.

In some embodiments, the address 206 may act as a primer target region complementary to a primer molecule. In such embodiments, a suitable primer molecule may be used to amplify the nucleic acid molecules associated with a given address 206, so that the probability can be increased that any given molecule within an aliquot is associated with the given address 206. To further increase the rate of amplification, a reverse sequence representing the address may also be present at the tail end of each molecule so that the primer molecule may attach to both ends. In the illustrated molecules 212-216, this reverse address is illustrated in broken line, because it is optional.

Figure 3:
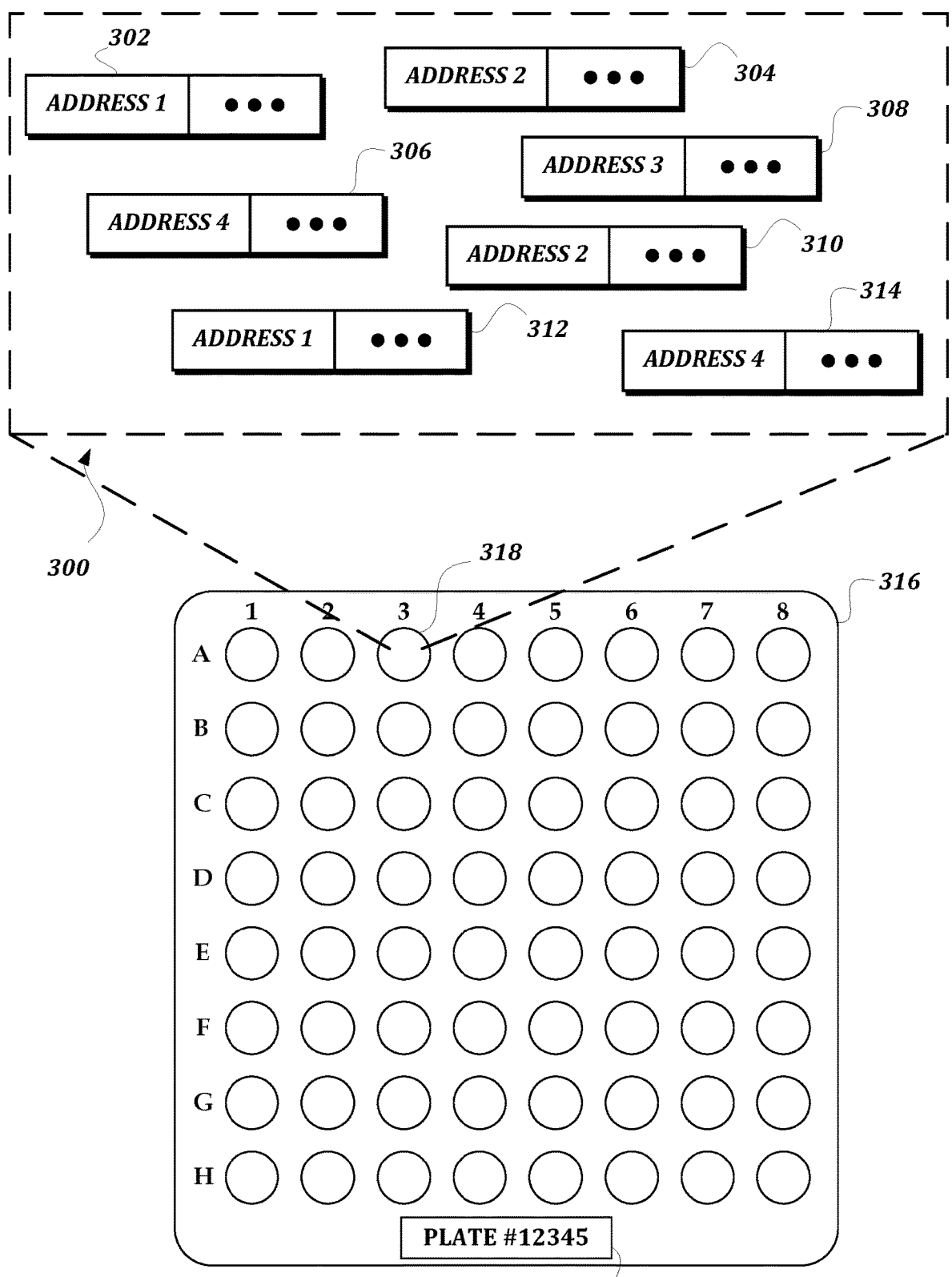
FIG. 3 is a schematic diagram that illustrates an exemplary embodiment of storage of nucleic acid molecules in an exemplary nucleic acid library according to various aspects of the present disclosure.

FIG. 3 is a schematic diagram that illustrates an exemplary embodiment of storage of nucleic acid molecules in an exemplary nucleic acid library according to various aspects of the present disclosure. As shown, the nucleic acid library 126 includes a well plate 316. The well plate 316 may be only one of many well plates within the nucleic acid library 126. As such, the well plate 316 is identified by a well plate identifier 320. Further, each well on the well plate 316 may be identified by a letter and a number on a grid, such as the well 318 identified by the code "A3." The well plate identifier 320 and the well grid location may be combined to create a physical location identifier within the nucleic acid library 126. One benefit of some embodiments of the present disclosure is the ability to randomly access addresses within the nucleic acid library 126. Arranging the molecules according to physical location identifiers within the nucleic acid library 126 is one example of a technique usable to allow random access.

In some embodiments, the contents 300 of each physical location, such as the well 318, may include a plurality of nucleic acid molecules 302-314. In some embodiments, the contents 300 of a given physical location may include nucleic acid molecules associated with more than one address. For example, as shown, molecules 302 and 312 are associated with address 1, molecules 304 and 310 are associated with address 2, molecule 308 is associated with address 3, and molecules 306 and 314 are associated with address 4. In some embodiments, all of the molecules 302-314 within an aliquot drawn from the contents 300 may be sequenced to retrieve a value associated with a given address, and the data associated with non-matching addresses is discarded. In some embodiments, amplification may be used for a given address, thereby increasing the chance that mostly (or only) molecules associated with the given address will be sequenced even if the molecules 302-314 in an aliquot drawn from the contents 300 initially include molecules with many different addresses.

FIG. 3 shows a well plate 316 for ease of illustration, though one or ordinary skill in the art will recognize that in other embodiments, any other type of container capable of storing nucleic acid molecules at locations identified by physical location identifiers may be used. Furthermore, the nucleic acids can be stored in any configuration, or in conjunction with any known medium that can facilitate storage and preservation of the nucleic acids. For example, as described above, the nucleic acids can be stored in the nucleic acid storage library 126 in association with solid supports, such as beads or microarrays. For example, the nucleic acid molecules can be immobilized on solid supports in spatially defined physical locations that can be addressed separately from other nucleic acid molecules also stored in the nucleic acid storage library 126. In some embodiments, the stored nucleic acids are lyophilized and can be addressed or accessed by hydrating or reconstituting the nucleic acids and removing an aliquot for amplification, sequencing, and/or other analysis. In some embodiments, the nucleic acids are stored in the presence of nuclease inhibitors known in the art to prevent premature degradation.

Figure 4A:
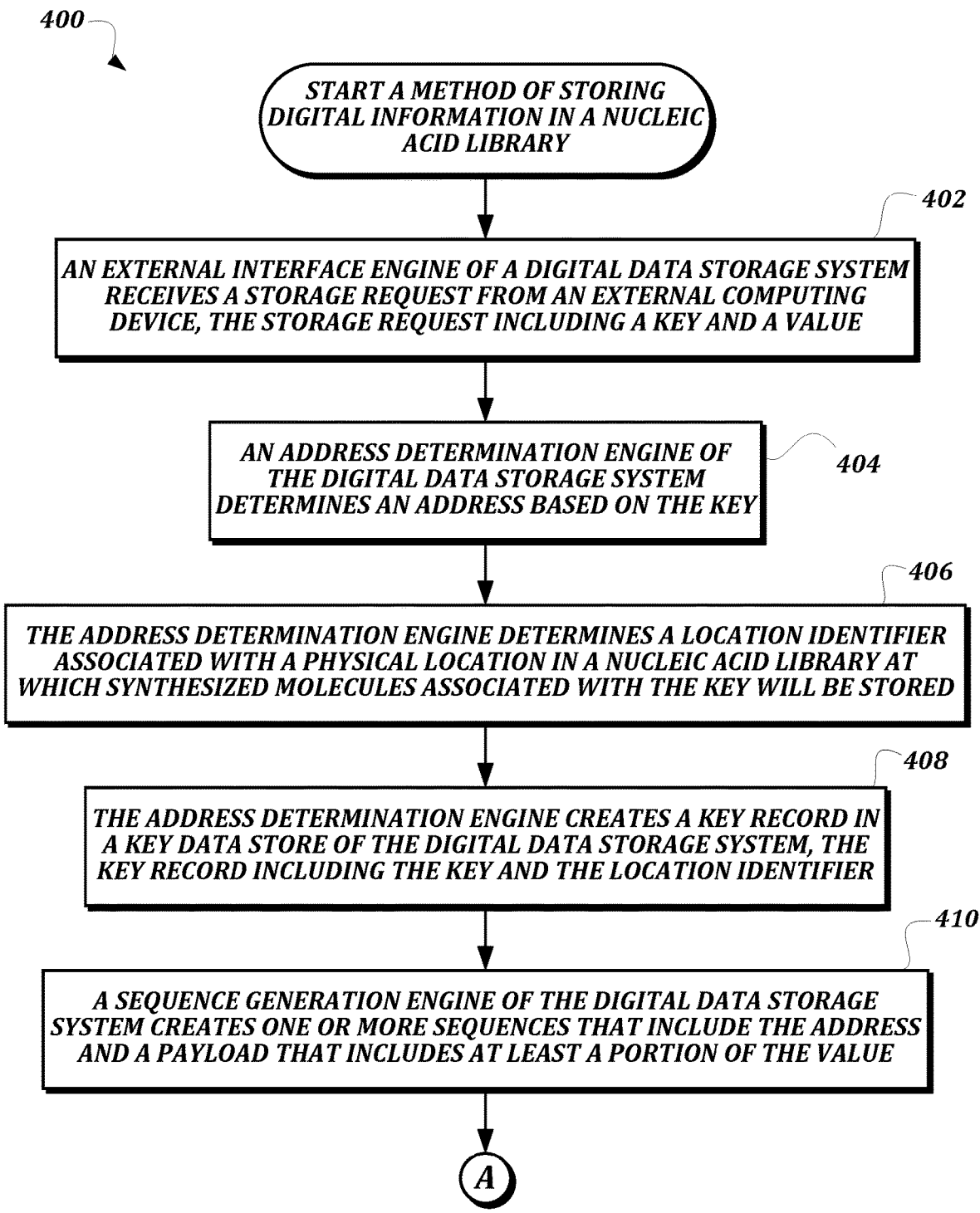
FIGS. 4A-4B are a flowchart that illustrates an exemplary embodiment of a method of storing digital information in a nucleic acid library according to various aspects of the present disclosure.
Figure 4B:
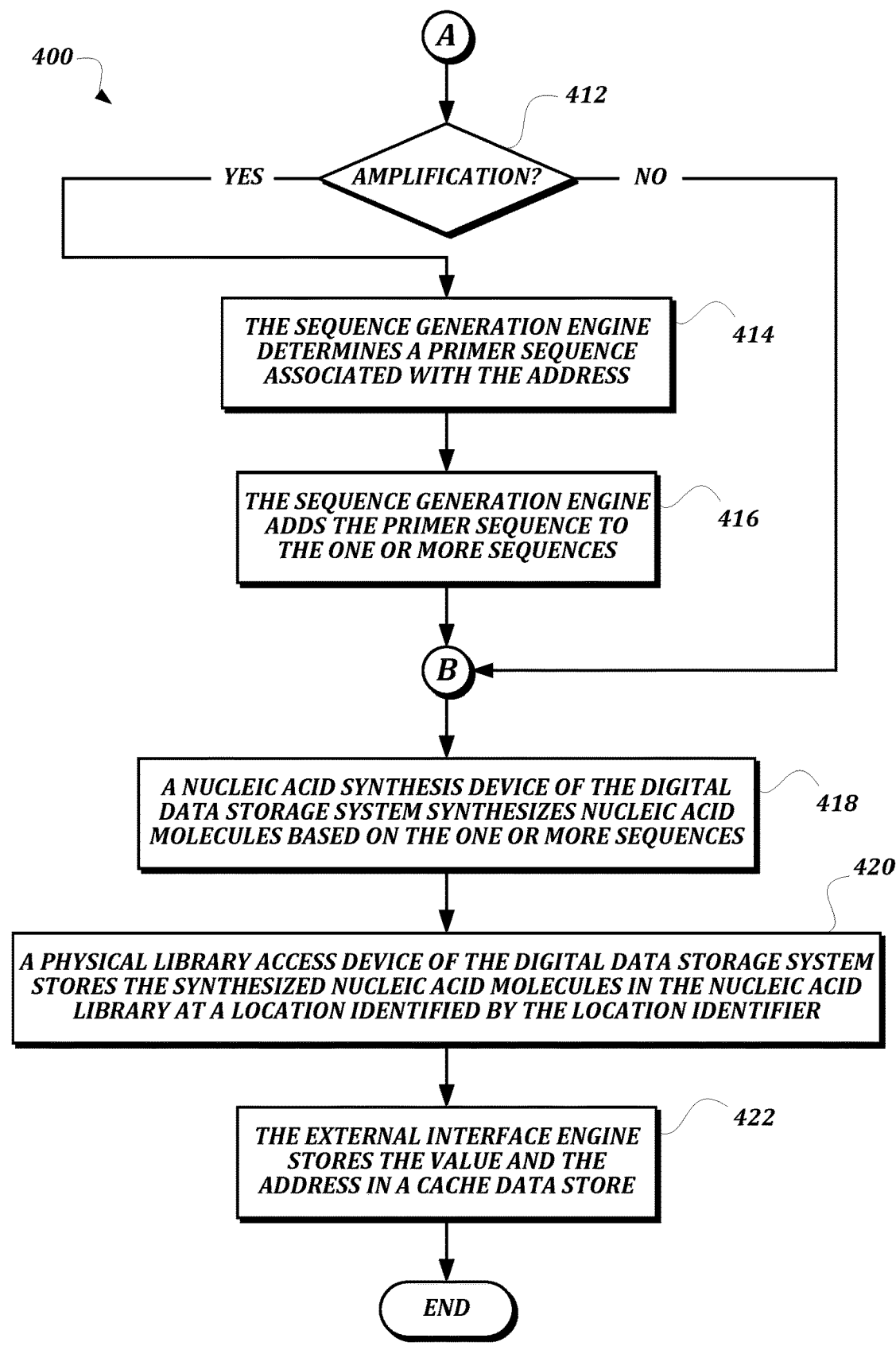

FIGS. 4A-4B are a flowchart that illustrates an exemplary embodiment of a method of storing digital information in a nucleic acid library according to various aspects of the present disclosure. From a start block, the method 400 proceeds to block 402, where an external interface engine 108 of a digital data storage system 100 receives a storage request from an external computing device 102, the storage request including a key and a value. As discussed above, the storage request may be received via an API, an input into a GUI, or via any other suitable technique. Further, the key and the value may each be any type of digital data. In some embodiments, the external interface engine 108 may perform checks on the key and/or value to ensure that the data is appropriate for use by the digital data storage system 100. For example, in some embodiments, the external interface engine 108 may check to see if the key conforms with a maximum size or data type requirement, such as confirming that the key is a string of less than a maximum length, an integer of less than a maximum value, and/or the like. In some embodiments, the external interface engine 108 may check the key data store 112 to determine whether the key has been previously used, and may reject the storage request if the key has previously been used.

At block 404, an address determination engine 110 of the digital data storage system 100 determines an address based on the key. In some embodiments, the address may be the key itself. For example, if the key is an integer below a size threshold, and the size threshold matches the number of addresses available, then the key may be used interchangeably with the address. One such example is if the address is sized appropriately to fit a globally unique identifier (GUID), and the key supplied in the storage request is a GUID, then the key may be used directly as the address. In some embodiments, a variable length key from a large set of possible keys could be hashed to fit within a smaller address space or to otherwise generate fixed-length addresses. For example, the key may be processed with a cryptographic hash function such as MD5, SHA-2, or the like, a non-cryptographic hash function, or any other hash function, in order to transform variable length data within a key to a fixed length address. In some embodiments such as those described above, mapping between key and address may be deterministic, and the address may be determined from the key with no other information. In some embodiments, an address may be randomly paired with a given key, and a record of the key-address mapping is stored in the key data store 112.

At block 406, the address determination engine 110 determines a location identifier associated with a physical location in a nucleic acid library 126 at which synthesized molecules associated with the key will be stored. As illustrated and described above, the location identifier may uniquely identify a well plate and/or a well within a well plate. In other embodiments, other nucleic acid storage technologies or configurations may instead be used, and the location identifier would be adapted accordingly as understood by one of ordinary skill in the art. The location identifier and physical location within the nucleic acid library 126 to be used may be determined using any suitable technique. In some embodiments, the address determination engine 110 may determine which physical locations are unused (or have been used the fewest number of times), and may choose a location based on that determination. In some embodiments, the address determination engine 110 may use a pseudorandom number generator to determine the location identifier, and may rely on the distribution of the random numbers to evenly distribute stored nucleic acid molecules through the physical locations. In some embodiments, the address determination engine 110 may determine the location based on a characteristic of the key or the address. For example, a deterministic mapping between the key and/or the address to the set of possible location identifiers may be established using a hash function and/or the like. At block 408, the address determination engine 110 creates a key record in a key data store 112 of the digital data storage system 100, the key record including the key and the location identifier. In embodiments wherein a deterministic mapping exists between the key and/or the address to the location identifier, the key record may not be created, as it would be redundant. One of ordinary skill in the art will recognize that, although the key record is described as including the key and the location identifier, the key record may include the address instead of or in addition to the key.

Next, at block 410, a sequence generation engine 114 of the digital data storage system 100 creates one or more sequences that include the address and a payload that includes at least a portion of the value. As discussed above, because each nucleic acid molecule may be limited to a maximum length between 100-150 nucleotides to increase the likelihood of successful synthesis and sequencing, a value that cannot be encoded within this length may be split between multiple payloads. As such, the sequence generation engine 114 may create a separate sequence for each payload that also includes a sub-address to indicate where in the value the particular payload belongs. In some embodiments, the sequence generation engine 114 may also include one or more error detection payloads within each sequence useful in determining whether the nucleic acid molecule has been faithfully sequenced. Such an error detection payload may be a sequence of between, for example, 10-50 nucleotides that, when sequenced, is diagnostic of a faithful amplification and sequencing.

In some embodiments, the sequence generation engine 114 may encode the digital data within the address and value, such that it can be represented by a sequence of nucleotides. Any suitable encoding algorithm may be used, including the "DNASTORE" approach to encoding the extended ASCII characters into canonical nucleotide sequences, known in the art and described in, for example, U.S. Pub. No. 2005/005396 to Bharadwaj, et al., incorporated herein by reference in its entirety. Thus, all kinds of data, including text, image, audio etc., can be encrypted into the nucleic storage medium. As part of the encoding process, the sequence generation engine 114 may insert error correction/detection data. For example, in some embodiments, the sequence generation engine 114 may include one or more error detection payloads within each sequence useful in determining whether the nucleic acid molecule has been faithfully sequenced. Such an error detection payload may be a sequence of between, for example, 10-50 nucleotides that, when sequenced, is diagnostic of a faithful amplification and sequencing.

The method 400 then proceeds to a continuation terminal ("terminal A"). From terminal A (FIG. 4B), the method 400 proceeds to a decision block 412, where a determination is made whether support for amplification is desired. In some embodiments of the method 500 illustrated and described below, amplification may be used to extract desired molecules from the nucleic acid library 126 and/or increase the chances of sequencing desired molecules versus undesired molecules. In other embodiments, amplification may not be used. To support amplification in method 500, method 400 selectively adds a primer sequence to each of the one or more sequences. Whether or not amplification is used may be a user configurable parameter in an embodiment that includes a nucleic acid amplification device 120, and the determination at decision block 412 may be based on the user configuration. In embodiments that do not include the nucleic acid amplification device 120, the determination at decision block 412 would be based on the absence of the nucleic acid amplification device 120 from the system 100.

If amplification is not being used in the method 400, then the result of the determination at decision block 412 is NO, and the method proceeds to a continuation terminal ("terminal B"). Otherwise, if amplification is being used in the method 400, then the result of the determination at decision block 412 is YES, and the method 400 proceeds to block 414, where the sequence determination engine 114 determines a primer sequence associated with the address. In some embodiments, the sequence determination engine 114 may hash the address to fit within a set of valid primer sequences before encoding the hashed value in a primer sequence. In some embodiments, the address may already be a hashed or otherwise processed version of the key that is intended to fit within the set of valid primer sequences, and so the sequence determination engine 114 may be able to simply encode the address to create the primer sequence. In some embodiments, the same primer sequence may be applied to all synthesized nucleic acid molecules in order to allow amplification of all molecules. In such embodiments, the address may not be used to determine the primer sequence.

At block 416, the sequence generation engine 114 adds the primer sequence to the one or more sequences that were created in block 410. The sequence generation engine 114 may add the primer sequence to the start of each sequence, to the end of each sequence, or both. The method 400 then proceeds to terminal B.

From terminal B, the method 400 proceeds to block 418, where a nucleic acid synthesis device 118 of the digital data storage system 100 synthesizes nucleic acid molecules based on the one or more sequences, as described above.

At block 420, a physical library access device 124 of the digital data storage system 100 stores the synthesized nucleic acid molecules in the nucleic acid library 126 at a location identified by the location identifier. The physical library access device 124 and nucleic acid library 126 are described in more detail above. As described, the nucleic acids can be stored in any appropriate medium and/or in any appropriate device to facilitate preservation of the nucleic acids.

Assuming the synthesized nucleic acid molecules were successfully stored in the nucleic acid library 126, the method 400 proceeds to block 422, where the external interface engine 108 stores the value and the address in a cache data store 106. The value and the address may be stored together in a single record in the cache data store 106 to allow a subsequent read request associated with the key or address to bypass the retrieval and sequencing of the nucleic acid molecules from the nucleic acid library 126. In some embodiments, the record may include a timestamp indicating when it was created. Once the cache data store 106, the timestamps of existing records may be used to determine which record to evict from the cache data store 106 in order to create storage space for a newly created record. In some embodiments, the cache data store 106 may not be present or used, and so block 422 is optional. The method 400 then proceeds to an end block and terminates.

Figure 5A:
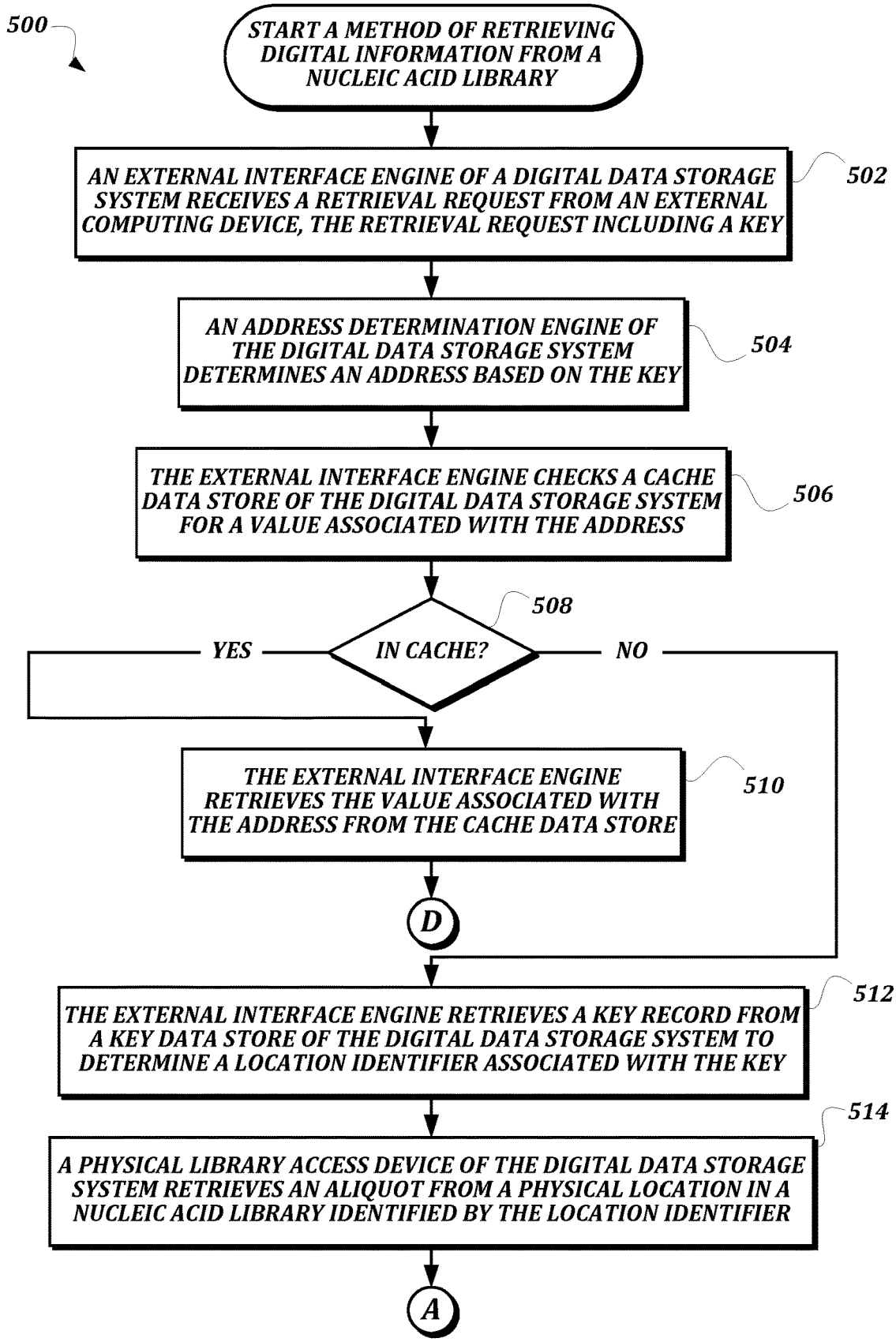
FIGS. 5A-5C are a flowchart that illustrates an exemplary embodiment of a method of retrieving digital information from a nucleic acid library according to various aspects of the present disclosure.
Figure 5B:
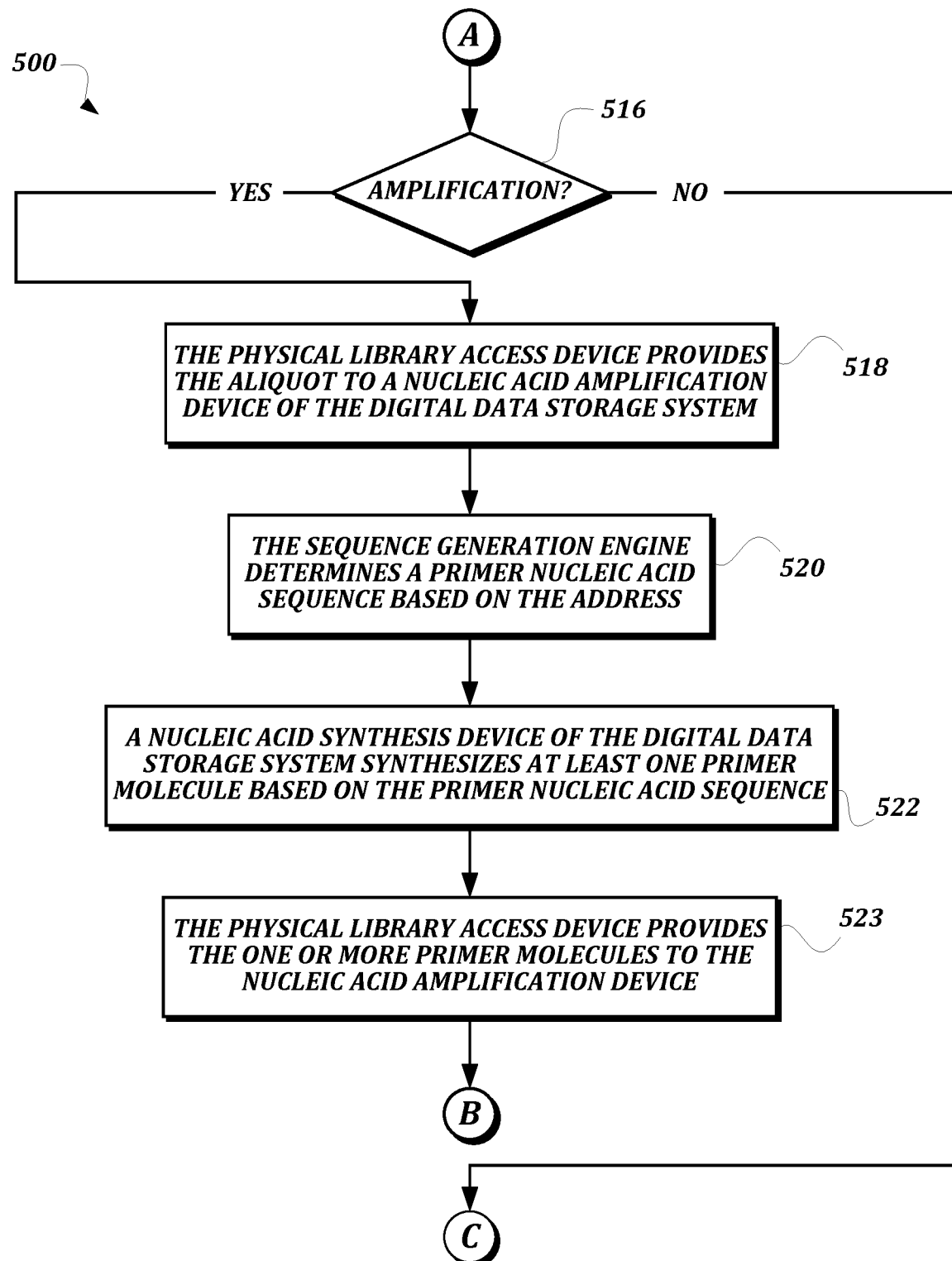
Figure 5C:
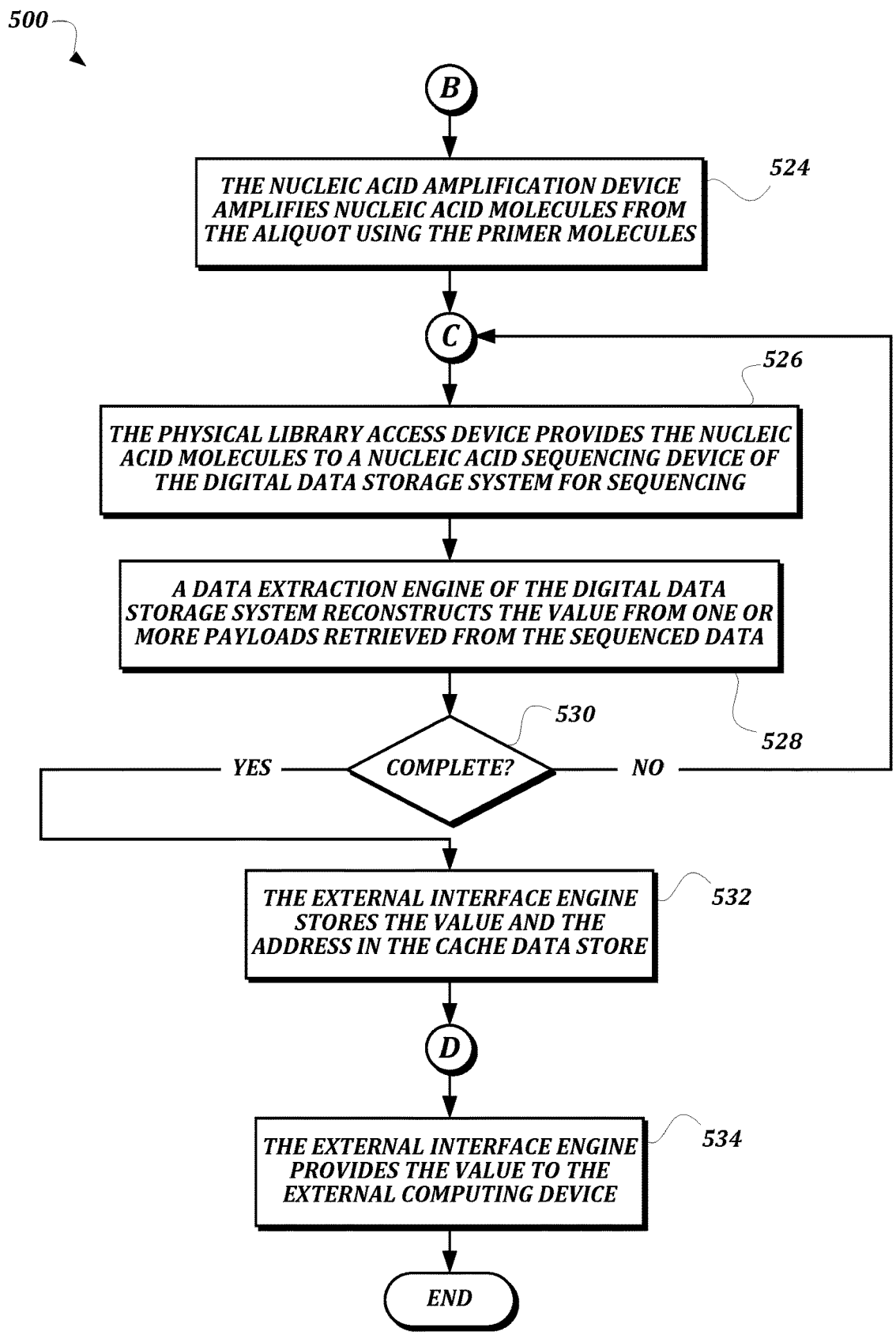

FIGS. 5A-5C are a flowchart that illustrates an exemplary embodiment of a method of retrieving digital information from a nucleic acid library according to various aspects of the present disclosure. From a start block, the method 500 proceeds to block 502, where an external interface engine 108 of a digital data storage system 100 receives a retrieval request from an external computing device 102, the retrieval request including a key. As discussed above, the retrieval request may be received via an API, an input into a GUI, or via any other suitable technique. Next, at block 504, an address determination engine 110 of the digital data storage system 100 determines an address based on the key. The determination of the address based on the key uses a technique that matches those discussed above with respect to block 404 in method 400, so that the same address is determined for the same key. A description of these techniques is not repeated here for the sake of brevity.

At block 506, the external interface engine 108 checks a cache data store 106 of the digital data storage system 100 for a value associated with the address. In some embodiments, the cache data store 106 may store values in association with keys instead of addresses, in which case the external interface engine 108 would use the key to check the cache data store 106 instead of the address.

The method 500 then proceeds to a decision block 508, where a determination is made based on whether a value associated with the address was found in the cache data store 106. If such a value was found, then the result of the determination at decision block 508 is YES, and the method 500 proceeds to block 510. At block 510, the external interface engine 108 retrieves the value associated with the address from the cache data store 106, and then proceeds to a continuation terminal ("terminal D"). In this way, the method 500 can improve read performance by bypassing the process of extracting and sequencing information from the nucleic acid library 126.

If a value associated with the address was not found in the cache data store 106, then the result of the determination at decision block 508 is NO, and the method 500 proceeds to block 512. In some embodiments, the cache data store 106 may not be present or used. Further, in some embodiments, the read request may include an indication regarding whether or not the cache data store 106 should be used, or whether instead the data should be retrieved from the nucleic acid library 126 regardless of whether it is also present in the cache data store 106. In such embodiments, the method 500 would proceed directly from block 504 to block 512.

At block 512, the external interface engine 108 retrieves a key record from a key data store 112 of the digital data storage system 100 to determine a location identifier associated with the key. In some embodiments, the external interface engine 108 may be able to derive the location identifier directly from the key or the address, and so may not need to consult the key data store 112 to determine the location identifier. Next, at block 514, a physical library access device 124 of the digital data storage system 100 retrieves an aliquot from a physical location in a nucleic acid library 126 identified by the location identifier. For example, the location identifier may identify the particular well of a particular plate of the nucleic acid library 126. The physical library access device 124 then removed an aliquot from the particular location (e.g., plate and well) using an automated pipetting mechanism. The method 500 then proceeds to a continuation terminal ("terminal A").

From terminal A (FIG. 5B), the method 500 proceeds to a decision block 516, where a determination is made regarding whether amplification is to be performed. As in method 400, the determination may be based on a user configuration or hardware present in the digital data storage system 100. If amplification is not to be performed, then the result of the determination at decision block 516 is NO, and the method 500 proceeds to a continuation terminal ("terminal C"). Otherwise, if amplification is to be performed, then the result of the determination at decision block 516 is YES, and the method 500 proceeds to block 518, where the physical library access device 124 provides the aliquot to a nucleic acid amplification device 120 of the digital data storage system 100. At block 520, the sequence determination engine 520 determines a primer nucleic acid sequence based on the address. The sequence determination engine 520 uses a similar technique to determine the primer nucleic acid sequence as those discussed above, such that the same sequence will be determined for the same address. As such, detailed discussion of the techniques used is not repeated here for the sake of brevity.

Next, at block 522, a nucleic acid synthesis device 118 of the digital data storage system 100 synthesizes at least one primer molecule based on the primer nucleic acid sequence. The at least one primer molecule is complementary to a primer target sequence in the nucleic acid molecules to be amplified. In some embodiments, generic primer molecules are used to amplify all contents of the aliquot, in which case they may either be taken from a store of primer molecules (instead of synthesized from constituent nucleotides), or may be synthesized from a given sequence that is not based on a particular address. In some embodiments, a plurality of the primer molecules is synthesized. The extent to primer molecule synthesis (i.e., how many primer molecules to synthesize) can be readily determined to securely provide sufficient primers in excess to ensure template amplification to the desired degree. At block 523, the physical library access device 124 provides the one or more primer molecules to the nucleic acid amplification device 120, and the method 500 then proceeds to a continuation terminal ("terminal B").

From terminal B (FIG. 5C), the method 500 proceeds to block 524, where the nucleic acid amplification device 120 amplifies nucleic acid molecules from the aliquot using the primer molecules. As described in more detail above, the nucleic acid amplification device 120 can be configured to amplify the nucleic acid obtained ultimately from the nucleic acid library 126 using the one or more primer molecules provided by the nucleic acid synthesis device 118. The nucleic acid amplification device 120 can amplify the nucleic acid according to any appropriate means, including the polymerase chain reaction (PCR), rolling circle replication, loop-mediated isothermal amplification (LAMP), helicase dependent amplification (HDA), and/or any other suitable technique. For example, in PCR, the nucleic acid amplification device 120 includes a PCR thermal cycler, which can alter the temperature of the solution to provide for the appropriate melting, annealing, and, optionally extension, conditions. As will be understood, the appropriate conditions provided by the nucleic acid amplification device 120 facilitates the primer molecules to anneal (base pair hybridize) to the corresponding sequence templates within the single stranded target nucleic acid and the extension of the primer molecule into a more full-length complement of the template sequence by an appropriate polymerase enzyme, as are well-known in the art.

The method 500 then proceeds to terminal C, and then to block 526, where the physical library access device 124 provides the nucleic acid molecules to a nucleic acid sequencing device 122 of the digital data storage system 100 for sequencing. As described above, the nucleic acid sequencing device 122 is configured to determine the order of nucleobases in a polynucleotide by any appropriate means, including, for example, chain termination (i.e., "Sanger") sequencing, chemical (i.e., "Maxam-Gilbert") sequencing, as well as next generation sequencing techniques. In some embodiments, the nucleic acid sequencing device 122 is configured to determine the order of nucleobases using nanopore-based polymer analysis. Nanopore-based analysis methods involve passing the nucleic acid analyte, for example single-stranded DNA ("ssDNA") template, through a nanoscopic opening while monitoring a signal, such as an electrical signal, that is influenced by the physical properties of the polymer subunits as the nucleic acid analyte passes through the nanopore opening. The nanopore optimally has a size or three-dimensional configuration that allows the polymer to pass only in a sequential, single file order. The passage of each discrete monomeric subunit of the polymer can be correlated with the monitored signal. Differences in the chemical and physical properties of each nucleotide subunit that makes up the polymer, for example, the nucleotides that compose an ssDNA, result in characteristic electrical signals that can identify each monomeric subunit as it passes through the nanopore. Nanopores, such as solid state nanopores and protein nanopores held within lipid bilayer membranes, have been heretofore used for analysis of DNA and RNA and, thus, provide the advantage of robust analysis even with low analyte copy numbers.

In some embodiments, the nucleic acid sequencing device 122 sequences the entire aliquot, including molecules that include the address sought, as well as any molecules contained therein that do not include the address sought. If amplification is used, a vast majority of the molecules in the aliquot will be associated with the address and, thus, the proportion of irrelevant or unsought sequences will be vastly minimized. As described in more detail below, in some embodiments only a portion of the molecules present in the aliquot are sequenced, such as when one or a sufficient number of molecules that include the address sought are sequenced. The determination of sufficiency can be based on a predetermined number or a prediction of sufficient coverage of the encoded information in association with the intended address. In other embodiment all or substantially all the molecules in the aliquot are sequences and, as described in more detail below, sequences associated with irrelevant or unsought addresses can be discarded or stored in cache memory, but are not further utilized for the initial retrieval.

In some embodiments, the probability of the nucleic acid sequencing device 122 to sequence the nucleic acid molecules associated with the sought address is enhanced. For example, as described above, in some embodiments, the nucleic acid molecules associated with the sought addressed are amplified. In other, non-exclusive embodiments, the nucleic acid molecules associated with the sought address are isolated from other nucleic acids in the aliquot that are not associated with the sought address (e.g., are associated with a different, unsought address). For example, sequence-specific isolation techniques using isolation probes mounted to a solid support, which specifically hybridize to the nucleic acid molecules associated with the sought address, can be employed to isolate the relevant molecules for sequencing.

At block 528, a data extraction engine 116 of the digital data storage system 100 reconstructs the value from one or more payloads retrieved from the sequenced data. In some embodiments where both relevant and non-relevant nucleic acid molecules are included in the sequenced data, the data extraction engine 116 may filter out data associated with addresses other than the desired address. In some embodiments, the data extraction engine 116 may use the embedded error detection information to detect sequencing errors and discard data that cannot be verified. In some embodiments, the data extraction engine 116 may use indications within the sequenced data regarding encoding schemes that were used in order to decode the payload. In some embodiments, the data extraction engine 116 may use sub-addresses within the sequenced data to piece together a value that was split into multiple payloads.

Next, at decision block 530, a determination is made regarding whether sequencing is complete. In some embodiments, the determination may be based the address encoding and/or other header information, which is used to determine whether the entire value has been recovered. If the result of the determination at decision block 530 is NO, then the method 500 returns to terminal C for further processing. Otherwise, if the result of the determination at decision block 530 is YES, then the method 500 proceeds to block 532, where the external interface engine 108 stores the value and the address in a cache data store 106, using a technique similar to those discussed above with respect to block 422.

The method 500 then proceeds to terminal D, and then to block 534, where the external interface engine 108 provides the value to the external computing device 102. The value may be provided to the external computing device 102 via any suitable technique. In some embodiments, the same communication channel used to receive the retrieval request is used to provide the value to the external computing device 102. In some embodiments, a different communication channel may be used. For example, the value may be posted to a web page generated by the external interface engine 108, transmitted in an email generated by the external interface engine 108, or by any other suitable technique. The method 500 then proceeds to an end block and terminates.

Figure 6:
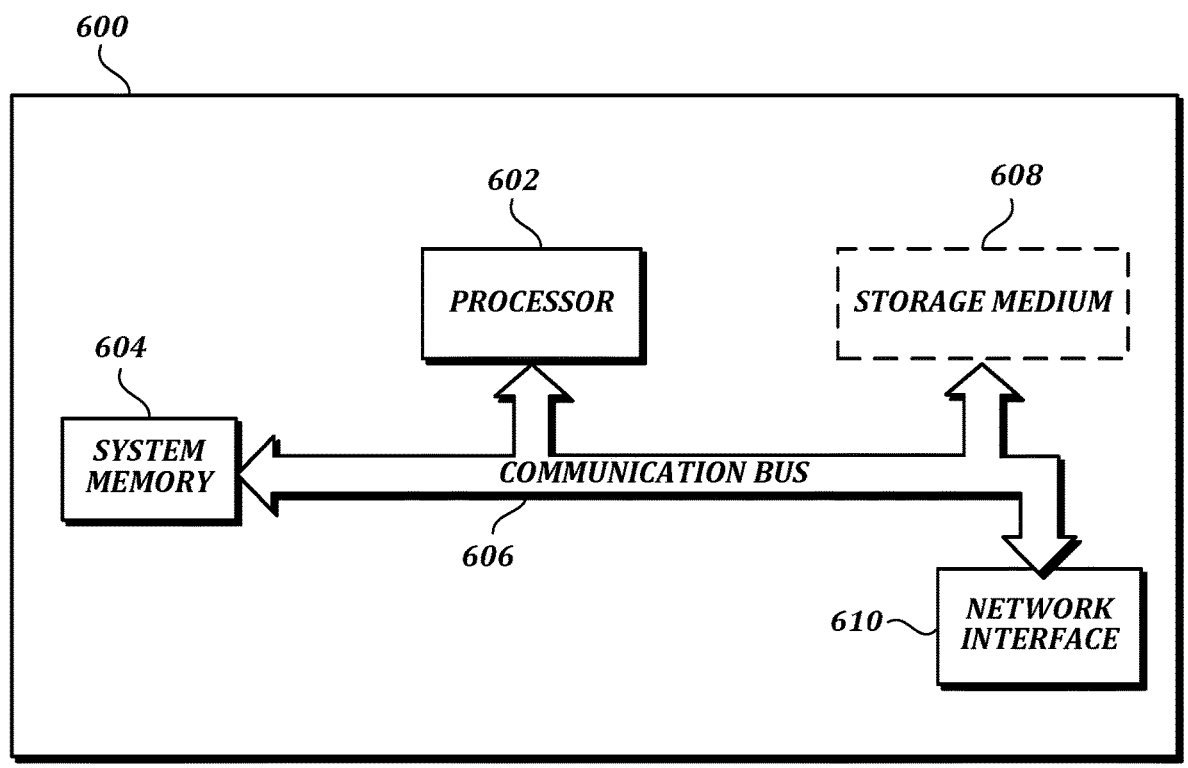
FIG. 6 illustrates aspects of an exemplary computing device appropriate for use with embodiments of the present disclosure.

FIG. 6 illustrates aspects of an exemplary computing device 600 appropriate for use with embodiments of the present disclosure. While FIG. 6 is described with reference to a computing device that is implemented as a device on a network, the description below is applicable to servers, personal computers, mobile phones, smart phones, tablet computers, embedded computing devices, and other devices that may be used to implement portions of embodiments of the present disclosure. Moreover, those of ordinary skill in the art and others will recognize that the computing device 600 may be any one of any number of currently available or yet to be developed devices.

In its most basic configuration, the computing device 600 includes at least one processor 602 and a system memory 604 connected by a communication bus 606. Depending on the exact configuration and type of device, the system memory 604 may include volatile or nonvolatile memory, such as read only memory ("ROM"), random access memory ("RAM"), EEPROM, flash memory, or similar memory technology. Those of ordinary skill in the art and others will recognize that system memory 604 typically stores data and/or program modules that are immediately accessible to and/or currently being operated on by the processor 602. In this regard, the processor 602 may serve as a computational center of the computing device 600 by supporting the execution of instructions.

As further illustrated in FIG. 6, the computing device 600 may include a network interface 610 comprising one or more components for communicating with other devices over a network. Embodiments of the present disclosure may access basic services that utilize the network interface 610 to perform communications using common network protocols such as TCP/IP, UDP, Ethernet, Token Ring, and/or the like. The network interface 610 may also include a wireless network interface configured to communicate via one or more wireless communication protocols, such as WiFi, 2G, 3G, LTE, WiMAX, Bluetooth, and/or the like.

In the exemplary embodiment depicted in FIG. 6, the computing device 600 also includes a storage medium 608. However, services may be accessed using a computing device that does not include means for persisting data to a local storage medium. Therefore, the storage medium 608 depicted in FIG. 6 is represented with a dashed line to indicate that the storage medium 608 is optional. In any event, the storage medium 608 may be volatile or nonvolatile, removable or nonremovable, implemented using any technology capable of storing information such as, but not limited to, a hard drive, solid state drive, CD ROM, DVD, or other disk storage, magnetic cassettes, magnetic tape, magnetic disk storage, and/or the like.

As used herein, the term "computer-readable medium" includes volatile and non-volatile and removable and non-removable media implemented in any method or technology capable of storing information, such as computer readable instructions, data structures, program modules, or other data. In this regard, the system memory 604 and storage medium 608 depicted in FIG. 6 are merely examples of computer-readable media.

Suitable implementations of computing devices that include a processor 602, system memory 604, communication bus 606, storage medium 608, and network interface 610 are known and commercially available. For ease of illustration and because it is not important for an understanding of the claimed subject matter, FIG. 6 does not show some of the typical components of many computing devices. In this regard, the computing device 600 may include input devices, such as a keyboard, keypad, mouse, microphone, touch input device, touch screen, tablet, and/or the like. Such input devices may be coupled to the computing device 600 by wired or wireless connections including RF, infrared, serial, parallel, Bluetooth, USB, or other suitable connections protocols using wireless or physical connections. Similarly, the computing device 600 may also include output devices such as a display, speakers, printer, etc. Since these devices are well known in the art, they are not illustrated or described further herein.

While illustrative embodiments have been illustrated and described, it will be appreciated that various changes can be made therein without departing from the spirit and scope of the invention. For example, while the methods described above refer to the movement of materials from one component to another using a physical library access device, in some embodiments separate components may be combined and/or provide outputs to and/or retrieve inputs from a common physical location. Accordingly, in such embodiments, the physical library access device may not be needed for the movement of materials between the components.

The embodiments of the invention in which an exclusive property or privilege is claimed are defined as follows:

1. A system for storing digital information in and retrieving digital information from a nucleic acid library, the system comprising:
a nucleic acid synthesis device;
a nucleic acid sequencing device;
the nucleic acid library; and
at least one computing device including a non-transitory computer-readable medium having instructions stored thereon, wherein the instructions are configured to cause the at least one computing device to provide:
an external interface configured to receive a read request, the read request including a first key;
an address determination engine configured to determine a first address based on the first key;
a sequence generation engine configured to:
determine a first primer sequence based on the first address; and
provide the first primer sequence to the nucleic acid synthesis device for synthesis of at least one first primer molecule; and
a data extraction engine configured to:
receive nucleic acid sequence information from the nucleic acid sequencing device representing nucleic acid molecules from the nucleic acid library as amplified using the at least one first primer molecule; and
extract a first value from the received nucleic acid sequence information, wherein the first value is associated with the first key;
wherein the nucleic acid library includes:
at least one nucleic acid molecule having a primer target region with a sequence complementary to the first primer sequence based on the first address and a region representing the first value; and
at least one nucleic acid molecule having a primer target region with a sequence complementary to a different primer sequence based on a different address and a region representing a different value.

2. The system of claim 1, wherein the external interface is further configured to receive a write request, the write request including a second key and a second value;
wherein the address determination engine is further configured to determine a second address based on the second key; and
wherein the sequence generation engine is further configured to:
determine a second primer sequence based on the second address;
generate at least one nucleic acid sequence that includes a primer target region and a region representing the second value, wherein the primer target region includes a sequence complementary to the second primer sequence; and
provide the at least one generated nucleic acid sequence to the nucleic acid synthesis device for synthesis of at least one nucleic acid molecule storing the second value to be stored in the nucleic acid library.

3. The system of claim 1, further comprising a physical library access device configured to store synthesized nucleic acid molecules in the nucleic acid library and to retrieve aliquots from the nucleic acid library.

4. The system of claim 3, further comprising a nucleic acid amplification device configured to amplify nucleic acid molecules using primer molecules.

5. The system of claim 4, wherein the physical library access device is further configured to:
retrieve an aliquot from the nucleic acid library; and
convey the aliquot to the nucleic acid amplification device for amplification using the at least one first primer molecule.

6. The system of claim 5, wherein the aliquot includes at least one nucleic acid molecule that includes a primer target region with a sequence complementary to the first primer sequence associated with the first key and at least one nucleic acid molecule that includes a primer target region with a sequence complementary to a different primer sequence associated with a different key.

7. The system of claim 3, further comprising a key data store configured to store a plurality of key records, wherein each key record is configured to store an association between a key and a physical location identifier associated with a physical location within the nucleic acid library.

8. The system of claim 7, wherein the physical library access device includes instructions configured to cause the physical library access device to store synthesized nucleic acid molecules in, and to retrieve aliquots from, physical locations in the nucleic acid library based on the physical location identifiers associated with the keys.

9. The system of claim 1, further comprising a housing that encloses at least the nucleic acid synthesis device, the nucleic acid sequencing device, and the at least one computing device.

10. A method of managing digital information stored in a nucleic acid library, the method comprising:
receiving, by a computing device, a read request including a first key;
calculating, by the computing device, a first primer sequence based on the first key;
providing, by the computing device, the first primer sequence to a nucleic acid synthesis device for synthesis of at least one first primer molecule;
receiving, by the computing device, nucleic acid sequence information from a nucleic acid sequencing device representing nucleic acids from the nucleic acid library amplified using the at least one first primer molecule, wherein the nucleic acid library includes at least one nucleic acid molecule having a primer target region with a sequence complementary to the first primer sequence based on the first key and at least one nucleic acid molecule having a primer target region with a sequence complementary to a different primer sequence based on a different key;
extracting, by the computing device, a first value associated with the first key from the received nucleic acid sequence information; and
transmitting, by the computing device, the first value in response to the read request.

11. The method of claim 10, wherein extracting the first value associated with the first key from the received nucleic acid sequence information includes verifying error detection information.

12. The method of claim 10, further comprising:
receiving, by the computing device, a write request including a second key and a second value;
calculating, by the computing device, a second primer sequence associated with the second key;
generating, by the computing device, at least one nucleic acid sequence that includes a second primer target region and a region representing the second value, wherein the second primer target region represents a sequence complementary to the second primer sequence; and
providing, by the computing device, the at least one nucleic acid sequence that includes the second primer target region and the region representing the second value to the nucleic acid synthesis device for synthesis of at least one nucleic acid molecule.

13. The method of claim 12, wherein generating at least one nucleic acid sequence that includes the second primer target region and the region representing the second value includes inserting error detection information within the region representing the second value.

14. A nontransitory computer-readable medium having computer-executable instructions stored thereon that are configured to, in response to execution by one or more processors of a computing device, cause the computing device to perform actions for managing digital information stored in a nucleic acid library, the actions comprising:
receiving, by the computing device, a write request including a first key and a first value;
calculating, by the computing device, a first primer sequence associated with the first key;
generating, by the computing device, at least one nucleic acid sequence that includes a first primer target region and a region representing the first value, wherein the first primer target region represents a sequence complementary to the first primer sequence; and
providing, by the computing device, the at least one nucleic acid sequence that includes the first primer target region and the region representing the first value to a nucleic acid synthesis device for synthesis of at least one nucleic acid molecule to be stored in the nucleic acid library.

15. The computer-readable medium of claim 14, wherein generating at least one nucleic acid sequence that includes the first primer target region and the region representing the first value includes inserting error detection information within the region representing the first value.

16. The computer-readable medium of claim 14, wherein the actions further comprise:
receiving, by a computing device, a read request including a second key;
calculating, by the computing device, a second primer sequence based on the second key;
providing, by the computing device, the second primer sequence to the nucleic acid synthesis device for synthesis of at least one second primer molecule;
receiving, by the computing device, nucleic acid sequence information from a nucleic acid sequencing device representing nucleic acids from the nucleic acid library amplified using the at least one second primer molecule;
extracting, by the computing device, a second value associated with the second key from the received nucleic acid sequence information; and
transmitting, by the computing device, the second value in response to the read request.

17. The computer-readable medium of claim 16, wherein the nucleic acid library includes nucleic acid molecules having primer target regions with sequences that are complementary to the second primer molecule and nucleic acid molecules having primer target regions with sequences that are not complementary to the second primer molecule but are complementary to another primer molecule.

18. The computer-readable medium of claim 16, wherein extracting the second value associated with the second key from the received nucleic acid sequence information includes verifying error detection information.

* * * * *